US010349943B2

(12) United States Patent
Noonan et al.

(10) Patent No.: US 10,349,943 B2
(45) Date of Patent: Jul. 16, 2019

(54) SYSTEM FOR PERFORMING EXTRALUMINAL CORONARY BYPASS AND METHOD OF OPERATION THEREOF

(71) Applicant: KONINKLIJKE PHILIPS N.V., Eindhoven (NL)

(72) Inventors: David Paul Noonan, New York, NY (US); Aleksandra Popovic, Boston, MA (US); Ralf Seip, Carmel, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 122 days.

(21) Appl. No.: 15/118,931

(22) PCT Filed: Feb. 13, 2015

(86) PCT No.: PCT/IB2015/051071
§ 371 (c)(1),
(2) Date: Aug. 15, 2016

(87) PCT Pub. No.: WO2015/128766
PCT Pub. Date: Sep. 3, 2015

(65) Prior Publication Data
US 2016/0354087 A1    Dec. 8, 2016

Related U.S. Application Data

(60) Provisional application No. 61/944,790, filed on Feb. 26, 2014.

(51) Int. Cl.
*A61B 17/11*    (2006.01)
*A61B 17/128*    (2006.01)
(Continued)

(52) U.S. Cl.
CPC .......... *A61B 17/11* (2013.01); *A61B 17/1285* (2013.01); *A61B 17/22012* (2013.01);
(Continued)

(58) Field of Classification Search
CPC ................. A61B 17/11; A61B 17/122; A61B 2017/1107; A61B 2017/1135;
(Continued)

(56) References Cited

U.S. PATENT DOCUMENTS

2003/0040736 A1    2/2003  Stevens
2003/0236542 A1*  12/2003  Makower ............. A61B 1/3137
606/167
(Continued)

FOREIGN PATENT DOCUMENTS

EP      1591069 A1    11/2005
WO   2012088501 A2     6/2012
(Continued)

*Primary Examiner* — Vi X Nguyen

(57) ABSTRACT

An apparatus that performs a bypass procedure includes a steerable body portion and at least one transducer controlled by at least one controller. The system may include one or more acts of transluminally detaching at least a portion of a first artery from connective tissue of a chest wall that is attached to the first artery by applying ultrasound signals of a first type emitted by the at least one transducer situated within the first artery; steeling the detached portion of the first artery from a current location to a bypass location by applying a force from the steerable body portion, which is located outside of the first artery, to at least a portion of the detached portion of the first artery; and coupling the first artery to a target artery at the bypass location to establish flow communication between the first artery and the target artery.

7 Claims, 7 Drawing Sheets

(51) Int. Cl.
- *A61B 17/22* (2006.01)
- *A61N 7/02* (2006.01)
- *A61B 18/20* (2006.01)
- *A61B 17/00* (2006.01)
- *A61B 17/122* (2006.01)
- *A61N 7/00* (2006.01)
- *A61B 34/20* (2016.01)
- *A61B 17/34* (2006.01)
- *A61B 18/22* (2006.01)
- *A61B 17/12* (2006.01)
- *A61B 18/00* (2006.01)
- *A61F 2/07* (2013.01)

(52) U.S. Cl.
CPC ............... *A61N 7/02* (2013.01); *A61N 7/022* (2013.01); *A61B 17/122* (2013.01); *A61B 17/34* (2013.01); *A61B 18/22* (2013.01); *A61B 2017/003* (2013.01); *A61B 2017/00252* (2013.01); *A61B 2017/00398* (2013.01); *A61B 2017/1107* (2013.01); *A61B 2017/1135* (2013.01); *A61B 2017/12004* (2013.01); *A61B 2018/00595* (2013.01); *A61B 2018/205547* (2017.05); *A61B 2034/2051* (2016.02); *A61F 2/07* (2013.01); *A61N 2007/0043* (2013.01); *A61N 2007/0073* (2013.01); *A61N 2007/0078* (2013.01)

(58) Field of Classification Search
CPC ..... A61B 17/08; A61B 17/34; A61B 17/1285; A61B 2017/00398
See application file for complete search history.

(56) References Cited

U.S. PATENT DOCUMENTS

| | | |
|---|---|---|
| 2004/0133225 A1 | 7/2004 | Makower |
| 2009/0230823 A1 | 9/2009 | Kushculey |
| 2010/0030063 A1* | 2/2010 | Lee .......................... A61B 5/06 600/424 |
| 2010/0069820 A1 | 3/2010 | Zotz |
| 2010/0198241 A1 | 8/2010 | Gerrah |
| 2011/0144438 A1 | 6/2011 | Paolitto |
| 2014/0005706 A1 | 1/2014 | Gelfand |
| 2015/0025518 A1 | 1/2015 | Kobayashi |

FOREIGN PATENT DOCUMENTS

| | | |
|---|---|---|
| WO | 2012120495 A2 | 9/2012 |
| WO | 2015128751 A1 | 9/2015 |
| WO | 2015128817 A1 | 9/2015 |

* cited by examiner

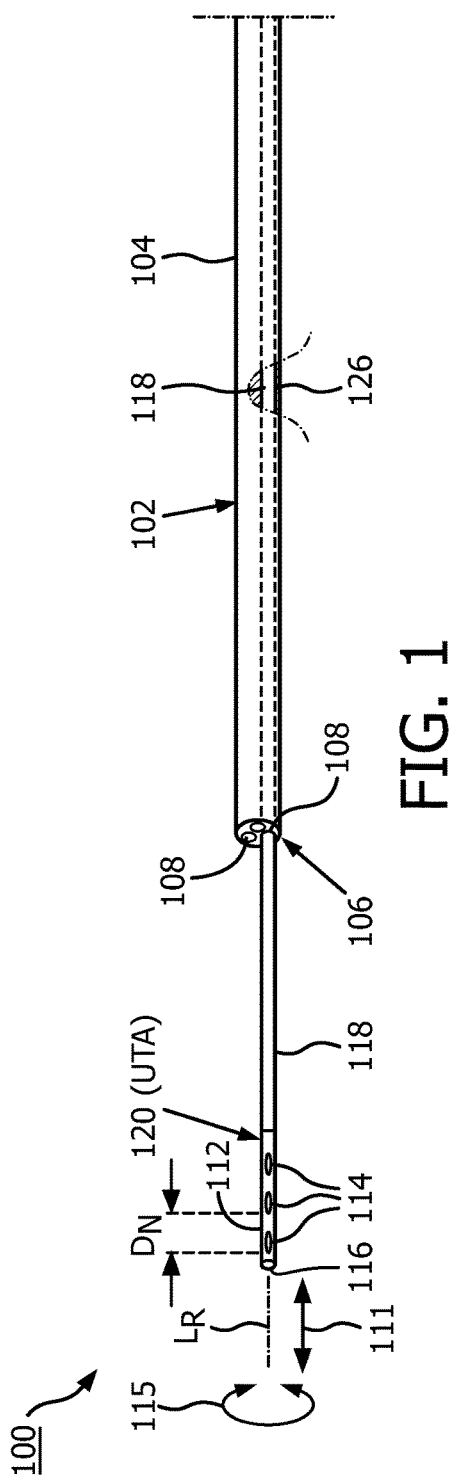
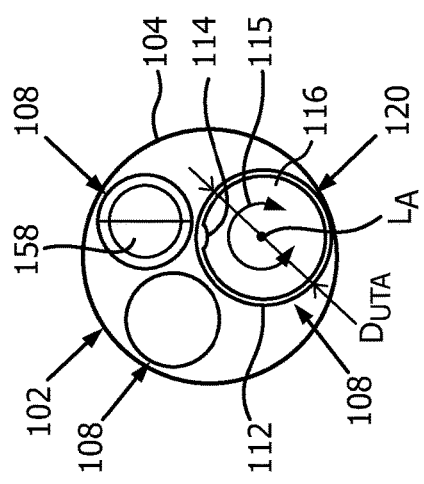

SYSTEM FOR PERFORMING EXTRALUMINAL CORONARY BYPASS AND METHOD OF OPERATION THEREOF

CROSS-REFERENCE TO PRIOR APPLICATIONS

This application is the U.S. National Phase application under 35 U.S.C. § 371 of International Application No. PCT/IB2015/051071, filed on Feb. 13, 2015, which claims the benefit of U.S. Provisional Patent Application No. 61/944,790, filed on Feb. 26, 2014. These applications are hereby incorporated by reference herein.

The present system relates to system for performing revascularization and, more particularly, to a system for performing an extraluminal myocardial revascularization using an artery such as a left internal mammary artery (LIMA) that is harvested using transluminal cauterization technique, and a method of operation thereof.

Coronary artery disease is caused by plaque build-up in the coronary arteries supplying blood to the heart muscle. As the result, oxygenation of the muscle is insufficient, resulting in chronic angina and myocardial infarction. Coronary revascularization is a procedure to re-establish the blood flow to the heart muscle. In percutaneous coronary intervention, stents are placed in the diseased areas to open up the artery. In bypass surgery, a new conduit is proximally attached to the aorta or other undiseased vessel and distally to the coronary artery thus bypassing the plaque. The most patent conduit is the left internal mammary artery (LIMA). LIMA supplies blood from the aorta to the chest muscles. Due to its patency, LIMA may be used to bypass the Left Anterior Descending artery (LAD), which supplies 60% of blood to the left ventricle. Such procedures are known as LIMA-to-LAD (LIMA-LAD) bypass and have significantly better outcomes when compared to any other revascularization technique such as surgical bypass with harvested veins or percutaneous stenting.

Despite its efficacy in terms of reducing risk from major cardiovascular events, open surgery LIMA-LAD bypass is currently performed significantly less frequently than stenting due to the invasiveness of the procedure. Similarly, while minimally invasive LIMA-LAD bypass is less invasive than open surgery, yet is more invasive than stenting and poses technical challenges for the surgeon.

When performing LIMA-LAD bypass using a minimally invasive surgery approach, a key challenge is how the LIMA is mechanically detached from the surrounding tissue given the limited workspace within the thoracic cavity, rigid instrumentation, limited visualization and the requirement to remove significant length of the vessel. During the removal process, these factors can lead to operator error and consequently damage of the vessel, which can limit its usefulness for grafting.

The system(s), device(s), method(s), arrangements(s), user interface(s), computer program(s), processes, etc. (hereinafter each of which will be referred to as system, unless the context indicates otherwise), described herein address problems in prior art systems.

In accordance with embodiments of the present system, there is disclosed a method of performing a coronary bypass procedure, the method may be performed by an apparatus which may include a steerable body portion and at least one transducer controlled by at least one controller, the method may include one or more acts of: transluminally detaching at least a portion of a first artery from connective tissue of a chest wall that is attached to the first artery by applying ultrasound signals of a first type emitted by the at least one transducer situated within the first artery; steering the detached portion of the first artery from a current location to a bypass location by applying a force from the steerable body portion, which is located outside of the first artery, to at least a portion of the detached portion of the first artery; and coupling the first artery to a target artery at the bypass location to establish flow communication between the first artery and the target artery.

It is also envisioned that the method may include an act of interrupting blood flow to the first artery by placing a clip about the first artery by the apparatus. It is also envisioned that the method may include an act of establishing a port in the target artery at the bypass location using one of an arterial puncture device and a laser arteriectomy device of the apparatus. In accordance with some embodiments, the act of coupling may further include an act of inserting a graft stent at least partially through the port in the target artery. In accordance with yet other embodiments, the method may include an act of transluminally cauterizing side branches of the first artery by applying ultrasound signals of a second type emitted by the at least one transducer that is situated within the first artery. In accordance with some embodiments, the ultrasound signals of the first type may include histotripsy pulses and the ultrasound signals of the second type may include high-intensity focused ultrasound (HIFU) pulses that are lower in intensity and longer in duration than the ultrasound signals of the first type. It is also envisioned that the first artery may be a left internal mammary artery (LIMA) and the target artery may be a left anterior descending artery (LAD) so as to achieve a LIMA-to-LAD bypass.

In accordance with embodiments of the present system, there is disclosed an apparatus for performing a surgical bypass procedure, the apparatus may include at least one controller which may be configured to: drive at least one transducer situated within a first artery to transluminally detach at least a portion of a first artery from connective tissue of a chest wall; steer a flexible portion of the surgical apparatus that is located outside of the first artery to move at least a portion of the detached portion of the first artery from a current location to a bypass location at a target artery (LAD); and/or couple the first artery to a target artery (LAD) at the bypass location to establish flow communication between the first artery and the target artery.

It is also envisioned that the at least one controller may be further configured to place a clip configured to interrupt blood flow about the first artery so as to interrupt blood flow through the first artery. It is also envisioned that the at least one controller may be further configured to establish a port in the target artery at the bypass location using one of an arterial puncture device and a laser arteriectomy device. Moreover, it is envisioned that the at least one controller may be further configured to insert a graft stent at least partially through the port in the target artery. It is also envisioned that the at least one controller may be further configured to transluminally cauterize side branches of the first artery by applying ultrasound signals of a second type emitted by the at least one transducer. It is also envisioned that the at least one controller may be further configured to drive the at least one transducer such that the ultrasound signals of the first type include histotripsy pulses and the ultrasound signals of the second type include high-intensity focused ultrasound (HIFU) pulses that are lower in intensity and longer in duration than the ultrasound signals of the first type.

In accordance with embodiments of the present system, there is disclosed a computer program stored on a computer readable memory medium, the computer program configured to control an apparatus including a steerable body portion and at least one transducer controlled by at least one controller to perform a surgical bypass procedure, the computer program may include a program portion configured to control the apparatus to transluminally detach at least a portion of a first artery from connective tissue of a chest wall that is attached to the first artery by applying ultrasound signals of a first type emitted by the at least one transducer situated within the first artery; steer the detached portion of the first artery from a current location to a bypass location by applying a force from the steerable body portion, which is located outside of the first artery, to at least a portion of the detached portion of the first artery; and/or couple the first artery to a target artery (LAD) at the bypass location to establish flow communication between the first artery and the target artery.

It is also envisioned that the program portion may be further configured to interrupt blood flow to the first artery by placing a clip about the first artery by a gripping portion of the apparatus. Moreover, it is envisioned that the program portion may be further configured to establish a port in the target artery at the bypass location using one of an arterial puncture device and a laser arteriectomy device. It is also envisioned that the program portion may be further configured to insert a graft stent at least partially through the port in the target artery. It is further envisioned that the program portion may be further configured to transluminally cauterize side branches of the first artery by applying ultrasound signals of a second type emitted by the at least one transducer. It is also envisioned that the ultrasound signals of the first type may include histotripsy pulses and the ultrasound signals of the second type may include high-intensity focused ultrasound (HIFU) pulses that are lower in intensity and longer in duration than the ultrasound signals of the first type.

The present invention is explained in further detail in the following exemplary embodiments and with reference to the figures, where identical or similar elements are partly indicated by the same reference numerals, and the features of various exemplary embodiments being combinable. In the drawings:

FIG. 1 shows a side view of a portion of a surgical apparatus in accordance with embodiments of the present system;

FIG. 2 shows an end view of a portion of the surgical apparatus similar as shown in FIG. 1 in accordance with embodiments of the present system;

Figure 4A:
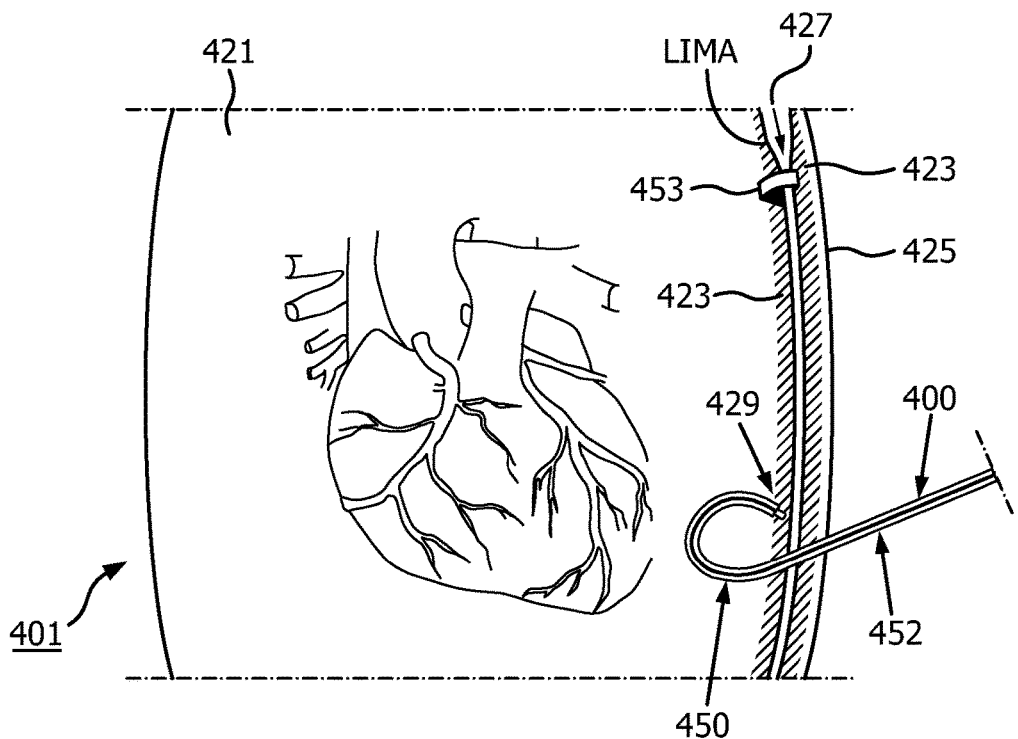
Figure 4B:
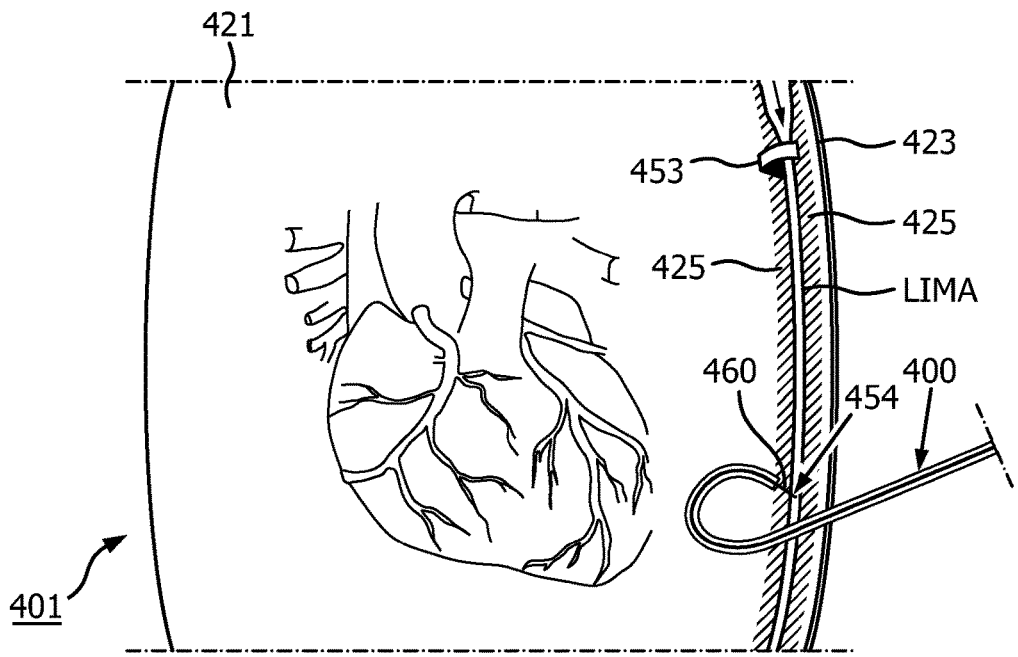
Figure 4C:
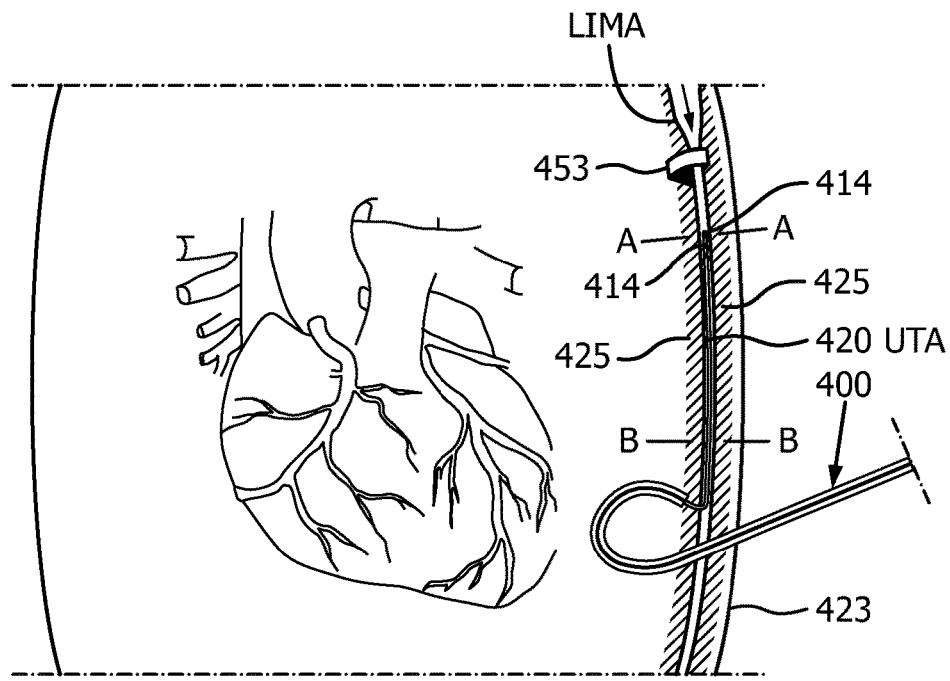

FIG. 4A which shows a surgical apparatus inserted into a thoracic cavity of a patient in accordance with embodiments of the present system;

FIG. 4B shows the surgical apparatus manipulating an arterial puncture device extended therefrom to puncture a LIMA at a determined puncture location in accordance with embodiments of the present system;

FIG. 4C shows the apparatus inserting a ultrasound transducer array device (UTA) 420 into the determined puncture location 454 and into the LIMA in accordance with embodiments of the present system.

Figure 4D:
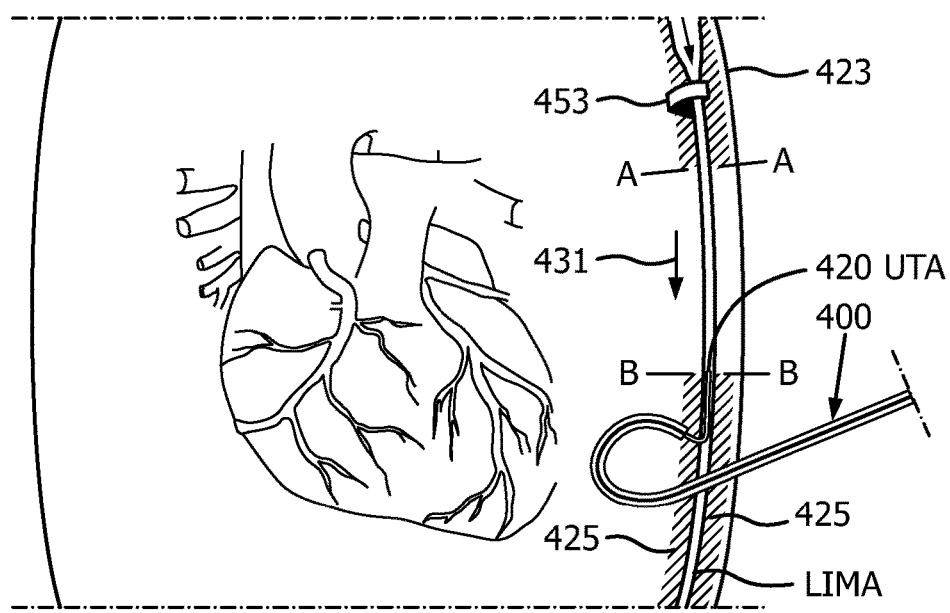
Figure 4E:
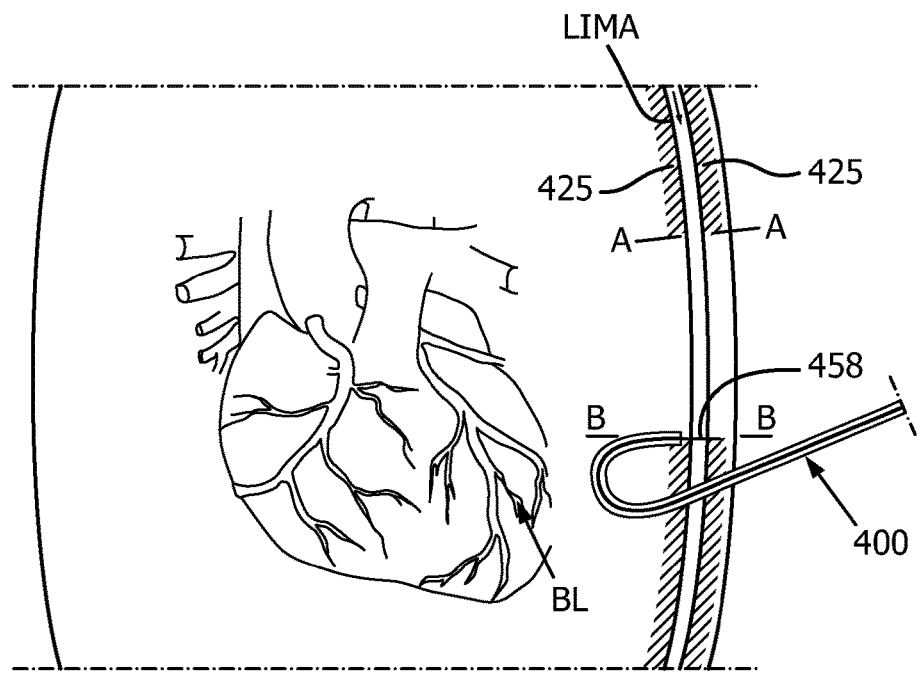
Figure 4F:
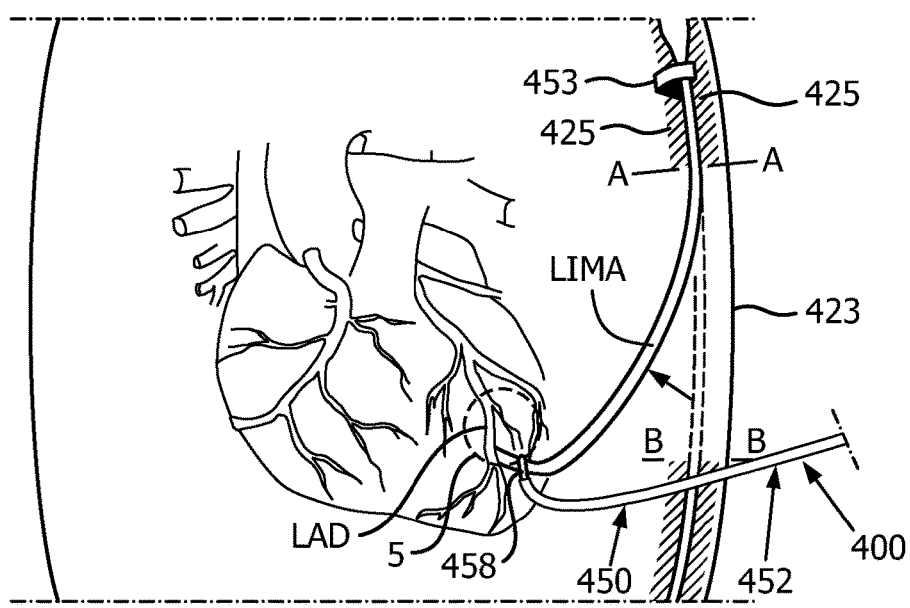
Figure 5:
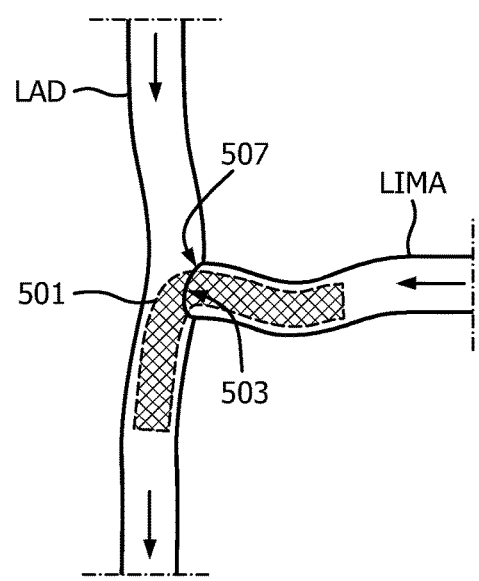
Figure 6:
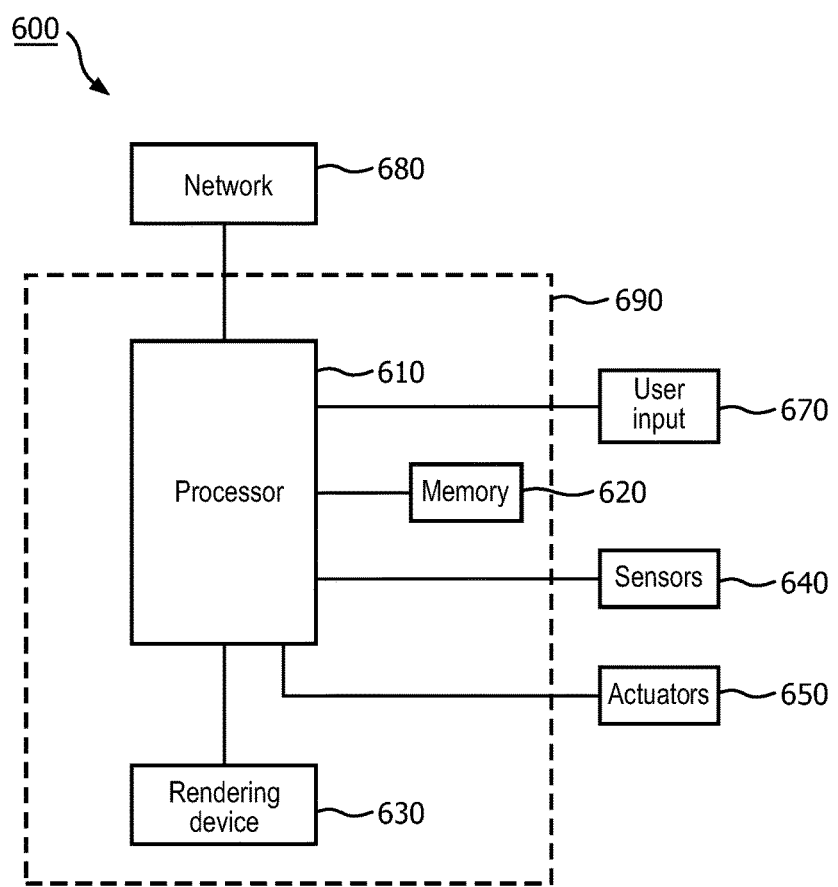

FIG. 4D shows the surgical apparatus withdrawing the UTA from the determined puncture location of the LIMA in accordance with embodiments of the present system;

FIG. 4E shows the apparatus grasping the LIMA near the distal end of the LIMA in accordance with embodiments of the present system;

FIG. 4F shows the apparatus placing the distal end of the LIMA at the desired bypass location on the LAD in accordance with embodiments of the present system;

FIG. 5 shows a detailed view of an interior portion of the coupling between the LIMA and the LAD in accordance with embodiments of the present system; and FIG. 6 shows a portion of a system in accordance with embodiments of the present system.

The following are descriptions of illustrative embodiments that when taken in conjunction with the following drawings will demonstrate the above noted features and advantages, as well as further ones. In the following description, for purposes of explanation rather than limitation, illustrative details are set forth such as architecture, interfaces, techniques, element attributes, etc. However, it will be apparent to those of ordinary skill in the art that other embodiments that depart from these details would still be understood to be within the scope of the appended claims. Moreover, for the purpose of clarity, detailed descriptions of well known devices, circuits, tools, techniques, and methods are omitted so as not to obscure the description of the present system. It should be expressly understood that the drawings are included for illustrative purposes and do not represent the entire scope of the present system. In the accompanying drawings, like reference numbers in different drawings may designate similar elements. Further, in some figures, cross-hatching may be omitted for the sake of clarity. The term and/or and formatives thereof should be understood to mean that only one or more of the recited elements may need to be suitably present (e.g., only one recited element is present, two of the recited elements may be present, etc., up to all of the recited elements may be present) in a system in accordance with the claims recitation and in accordance with one or more embodiments of the present system.

FIG. 1 shows a side view of a portion of a surgical apparatus 100 in accordance with embodiments of the present system. The surgical apparatus 100 may include a body 102 which may comprise a self-supporting, multi-segment, steerable device. For example, an actively steerable articulating instrument or a snake-like robot may be suitable for performing surgical procedures in accordance with embodiments of the present system. Steering actuators may be provided to actively steer portions of the body 102, if desired. The steering actuators may include electronic actuators controlled by a controller (e.g., including one of more processors, logic devices etc.), may be controlled by a user or may be controlled by a combination of the controller and the user to transmit a force to a corresponding portion of the body 102 to steer the body 102 in a desired direction and/or position the body in a desired orientation. A user interface (mechanical, electronic or mechanical and electrical) may be provided for a user to control portions of the tool such as the steering actuators directly (e.g., using mechanical couplings) and/or electronically (e.g., using a fly-by-wire (FBW)-type controls) under the control of the controller, if desired. In some embodiments, the user interface may include one or more of control knobs, levers, hard keys and/or soft keys (e.g., a portion of the user interface that may be flexibly programmed to invoke any of a number of functions).

The body 102 may include a proximal end and a distal end 106 and one or more internal channels 126 which may be configured to receive one or more instruments which may be passed through one or more of the internal channels 126 and may extend through corresponding openings such as openings 108 situated at the distal end 106 of the body 102.

The surgical apparatus 100 may include one or more instruments having corresponding functionalities. For example, in accordance with some embodiments, the surgical apparatus 100 may include one or more instruments such as: a puncture device configured to form a hole in at least one of a vessel of the patient, such as the LIMA and the LAD, a gripper configured to grip tissue (e.g., surgical pliers), a blood-flow restricting tool such as a balloon, a clip configured to interrupt blood flow through a vessel such as the LIMA, a stent deployment tool configured to deploy stents, a trans-catheter cauterizer configured to cauterize the side branches of vessel (e.g., the LIMA) using any suitable method such as transluminally, a stent installation tool configured to insert a stent such as a graft stent into a target artery, a camera configured to obtain two- or three-dimensional images (in real time), a coupling tool configured to couple tissue such as the LIMA to the LAD, and an ultrasound transducer array device (UTA) 120 configured to enable a vessel such as the LIMA to be removed from surrounding connective tissue (e.g., LIMA takedown), etc. The instruments may be passed through one or more of the internal channels 126 and may have a working end which extends through the opening 108 of a corresponding channel. Accordingly, one or more of the instruments may be slidably extended from the distal end 106 of the body 102 and/or may be retracted in a similar manner.

The UTA 120 may be configured to enable LIMA takedown as described in copending U.S. Patent application Ser. No. 15/119,077, filed Aug 15,2016, entitled "SYSTEM FOR PERFORMING TRANSLUMINAL CORONARY BYPASS AND METHOD OF OPERATION THEREOF" the contents of which are incorporated herein by reference. The UTA 120 may include passively-flexible catheter-like flexible body 118 which may have at least one ultrasonic transducer array 112 situated at a distal end 116 of the UTA 120 and which may include at least one transducer 114. The at least one transducer 114 may be driven by the controller to emit desired ultrasound signals, such as focused ultrasound signals in a desired location (e.g., a focal zone). For example, the desired location may be located beyond (e.g., outside of) a vessel wall of the LIMA. The ultrasound signals may include a series of ultrasound pulses.

Further, the UTA 120 may be configured such that at least the transducer array 112 may be rotated about a longitudinal axis (La) of the transducer array 112 relative to, for example, the body 102. At least one of the body 102 and the UTA 120 may be configured to slidably extend or retract the UTA 120 relative to the body 102 as illustrated by arrow 111. In some embodiments, the controller may control one or more of the rotation and/or extension/retraction of the UTA 120 relative to the body 102 so that a desired length of the LIMA may be separated from all connecting tissue. Accordingly, one or more actuators (e.g., rotary and/or linear motors, etc.) may be provided to rotate and/or extend/retract the UTA 120 relative to the body 102 under the control of the controller. However, in accordance with embodiments of the present system, a mechanical coupling may be provided for a user to rotate and/or extend/retract the UTA 120 relative to the body 102. In accordance with embodiments of the present system, location and/or orientation of the transducer array 112 may determined by sensors (e.g., see, FIG. 6, sensors 640) and provided to the controller for further processing. The controller may then use this information to determine position and/or orientation of the transducer array 112. This information may be used to determine movement of the transducer array 112 during use. For example, after the transducer array 112 is determined to rotate (e.g., by a rotational motor controlled by the controller) a full 360 degrees (or other amount e.g., 180, 720, etc.) while transducers 114 are driven to output a desired signal to fractionate at least one cylindrical region of connective tissue, the process may withdraw the transducer array 112 by a withdrawal distance (e.g., which may be limited to an inter transducer distance such as $D_w$) so that another cylindrical (e.g., an adjacent) region of connective tissue may be similarly fractionated. In yet other embodiments, as the transducers 114 of the transducer array 112 are driven and/or rotated about the longitudinal axis La, a back-and-forth motion as illustrated by the arrow 111 may be established by the controller and/or manually by the user. Thus, for example, in some embodiments, the movement of the transducer array 112 may be controlled by the controller based upon sensory information and/or operating instructions derived by a process of the surgical apparatus 100. However, in yet other embodiments, the movement of the transducer array 114 may be controlled by the user directly, via the controller using for example remote controls such as fly-by-wire controls or other suitable systems.

In accordance with embodiments of the present system, a real-time guidance system (e.g., a real-time guided imaging system such as an ultrasound, X-ray, computed tomography (CT), and/or magnetic resonance imaging (MRI) real-time guided imaging systems, or the like) may provide information related to a location and/or orientation of the surgical apparatus 100 relative to a body in which it is located in real time and form corresponding location information for the convenience of a user and/or for further processing by the system.

In accordance with some embodiments, one or more functionalities such as steering, puncturing, take-down, cauterizing, coupling, clipping, etc. of the surgical apparatus 100 are integrated in a single steerable surgical instrument which may be manually and/or autonomously controlled by a controller.

FIG. 2 shows an end view of a portion of the surgical apparatus 100 similar as shown in FIG. 1 in accordance with embodiments of the present system. The body 102 of the surgical apparatus 100 may have any suitable cross-sectional shape such as a round, substantially round, ovoid, or other suitable (e.g., suitable based on the system elements) cross-sectional shape. Similarly, the openings 108 and corresponding channels 126 may also have any suitable cross-sectional shape as above such as round, etc. For example, the UTA 120 may be configured such that its outside diameter ($D_{UTA}$) may be slightly smaller than an inside diameter of the LIMA so that a snug fit may be established. For example, in some embodiments the outside diameter of the UTA 120 ($D_{UTA}$) may be about 3 mm. However, other diameters are also envisioned. A grasping tool 158 (e.g., surgical pliers or other suitable tool for gripping tissue) is illustratively shown recessed in a corresponding channel.

A process of performing a bypass procedure to bypass a desired portion of a target artery using a graft artery will now be described. For the sake of clarity, it will be assumed that the graft artery is a LIMA and the target artery is a LAD. The following process will describe an extraluminal coronary bypass performed using any suitable surgical tool such as the surgical apparatus 100 or the like operating in accordance with embodiments of the present system. Although a LIMA-LAD coronary bypass is described, it is also envisioned that embodiments of the present system may be applied to perform other bypass procedures using other suitable vessels, destinations, etc., if desired.

Figure 3:
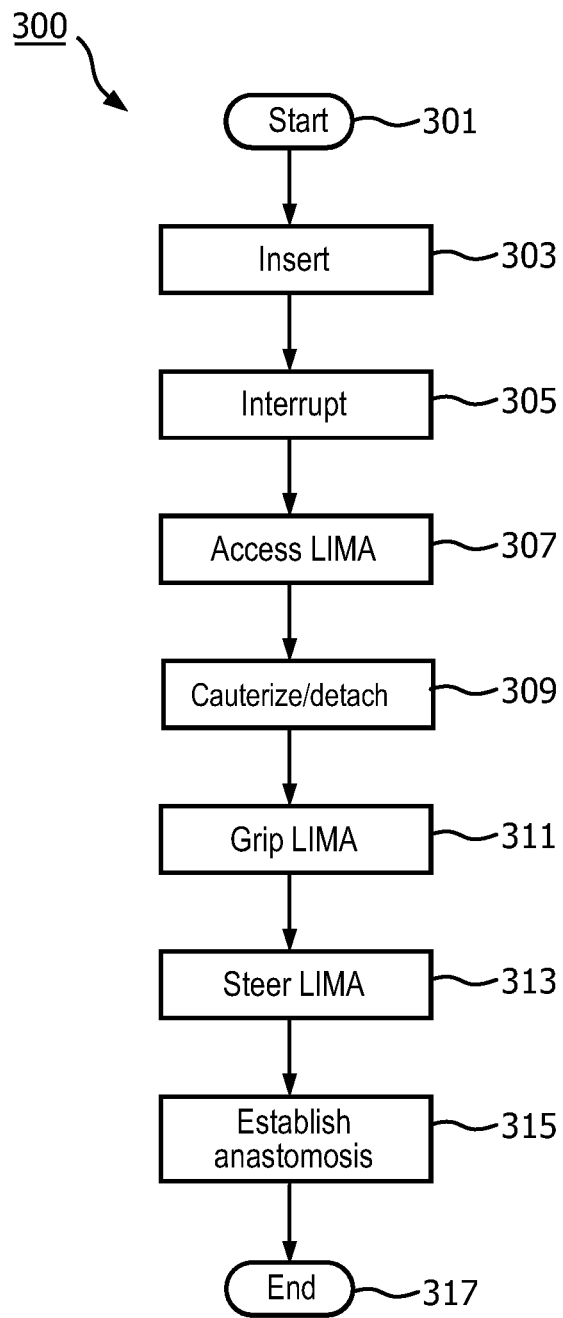
FIG. 3 is a flow diagram that illustrates a process performed by a system in accordance with embodiments of the present system.

FIG. 3 is a flow diagram that illustrates a process 300 performed by a system in accordance with embodiments of the present system. The process may perform an extraluminal revascularization process such as an extraluminal coronary bypass. The process 300 may be performed using one or more computers communicating over a network and may obtain information from, and/or store information to one or more memories which may be local and/or remote from each other. The process 300 may be performed using, inter alia, a flexible device such as the surgical apparatus 100 operating in accordance with embodiments of the present system and may include one of more of the following acts. Further, one or more of these acts may be combined and/or separated into sub-acts, if desired. Further, one or more of these acts need not be present, may be skipped (e.g., may be optionally available) for example depending upon embodiment, settings, what is desired, etc. In operation, the process may start during act 301 and then proceed to act 303.

During act 303, the surgical apparatus may be inserted into a thoracic cavity of a patient for example via a minimally invasive incision between the ribs and may be steered so as to engage its distal tip with the LIMA proximate to, or at, a location where the LIMA is determined to be removed from the cavity wall. This is illustrated in FIG. 4A which shows a surgical apparatus 400 (hereinafter apparatus for the sake of clarity) after insertion into a thoracic cavity 421 of a patient 401 in accordance with embodiments of the present system. The surgical apparatus 400 may be similar to the surgical apparatus 100. The surgical apparatus 400 may include portions 450, 452 such as a flexible portion 450 and a substantially rigid portion 452, each of which may be steered, directed, etc. The rigid portion 452 may be coupled to a base portion. In some embodiments, the base portion may include a robotic arm which may position and/or orientate the rigid portion 452 with a plurality of degrees of freedom (e.g., 6 degrees of freedom, etc.) under the control of a controller. Thus, the position and/or orientation of the rigid portion 452 and/or the flexible portion 450 may be controlled manually by a user and/or automatically by the controller, if desired, in accordance with user input and/or navigational-assisted surgical methods operating in accordance with embodiments of the present system.

The artery such as the LIMA may be identified using any suitable method such as by direct visual identification and/or using image recognition methods which analyze image information obtained from an imaging device (e.g., a camera) mounted at a distal end 429 of the apparatus 400. For example, the apparatus 400 may be an endoscope or laparoscope inserted through an incision in a patient 401. Image information may be rendered on a display of the system and/or may be provided to a controller of the system for further processing such for performing image processing methods to determine a location of the LIMA and/or other portions of the anatomy of the user. However, in yet other embodiments, the process may use any suitable navigation-assisted surgical imaging method which may locate the LIMA and the apparatus 400 in real-time and control the apparatus 400 so that its distal end 429 may be steered to be proximate to, or at, a location where the LIMA is desired to be removed from the cavity wall 425 and in a desired orientation (e.g., facing the LIMA from the backside of the chest wall 425 of the patient 401). In accordance with embodiments of the present system, the LIMA may also be identified using other imaging modalities such as X-ray, CT, or MRI. Accordingly, the apparatus 400 may be steered manually and/or automatically using, for example, a robotic/mechatronic interface to the location where the LIMA is desired to be removed from the cavity wall 425. Referring to FIG. 4A, the LIMA is illustratively shown attached to the chest wall 425 of the patient 401 by connective tissue 423 (illustratively shown as diagonal lines). A blood flow direction within the LIMA is illustrated by arrow 427. After completing act 303, the process may continue to act 305.

During act 305, the process may interrupt blood flow in the LIMA. Accordingly, a surgical clip 453 may be deployed through the surgical apparatus 400 (which may be steered accordingly) and attached to the LIMA. For example, a grasping tool (e.g., see, 458) of the apparatus 400 may be controlled by the controller to grip and place the surgical clip 453 about the desired vessel such as the LIMA and, once it is determined that the surgical clip is in position, the grasping tool may then release hold of the surgical clip 453. The surgical clip may include a biasing mechanism (e.g., a spring) and/or a locking mechanism (e.g., tabs, latches, etc.) to bias the surgical clip 453 about the LIMA so as to interrupt blood flow through the LIMA. The grasping tool and/or the surgical clip 453 may be passed through a channel of the apparatus. For example, when necessary to perform an act of the present system, the grasping tool may be extended from a channel of the apparatus 400. Conversely, when not necessary to perform an act of the present system, the grasping tool may be retracted into a channel of the apparatus and/or removed entirely from the channel, if desired.

In some embodiments, a balloon may be used to interrupt flow through the LIMA. For example, the apparatus 400 may puncture the LIMA (as will be described below) and thereafter a balloon may be inserted into the LIMA and thereafter inflated to interrupt blood flow in the LIMA (e.g., after puncturing the LIMA as will be described below). Further, in other embodiments if desired the balloon may be inserted proximate to the vessel and thereafter be inflated to interrupt blood flow. In any event, after completing act 305, the process may continue to act 307.

During act 307, the process may access the LIMA for example at a determined location such as a puncture location through use of an arterial puncture device passed through a channel of the surgical apparatus 400. For example, FIG. 4B shows the surgical apparatus 400 extending and manipulating an arterial puncture device 460 to puncture the LIMA at a determined puncture location 454 in accordance with embodiments of the present system. The puncture may extend through a wall of the LIMA and may be used to access the LIMA as will be described below. The puncture location 454 may be determined by a user and/or the process and may be downstream (relative to normal blood flow within the LIMA) of the surgical clip 453. After completing act 307, the process may continue to act 309.

During act 309, the process may insert an ultrasonic transducer array (such as the UTA 120 of FIG. 1) through the puncture and into the LIMA. Thereafter, the controller may direct, position and/or otherwise drive the at least one transducer of the UTA to transluminally cauterize side branches of the LIMA and/or to detach the LIMA from at least a portion of the surrounding connective tissue 423 using ultrasound signals such as ultrasound waves and/or ultrasound pulses. The UTA may include at least one ultrasonic transducer and may include a flexible body so that the UTA may be positioned and/or oriented as desired within the LIMA. For example, FIG. 4C shows the apparatus 400 inserting a UTA 420 into the determined puncture location 454 and into the LIMA in accordance with embodiments of the present system. Once the UTA 420 is inserted into the LIMA, the controller may drive a UTA to transmit focused ultrasound pulses (e.g., histotripsy pulses) from at least one ultrasonic transducer 414 of the UTA 420 to fractionate a desired portion including a length of connective tissue 425 such as connective tissue that lies between lines A-A and B-B in the present example.

In accordance with embodiments of the present system, the controller may control position and/or orientation of the UTA 420 so that selected connective tissue 425 of the chest wall 423 which may surround the LIMA which is located along a selected disconnect path (e.g., between, for example, lines A-A and B-B) may be fractionated so that the LIMA may be easily removed from the portion of the fractionated connective tissue 425. In accordance with embodiments of the present system, some connective tissue may remain attached to the LIMA when the LIMA is removed from the portion of the fractionated connective tissue.

The controller may be operative to rotate the UTA 420 about its longitudinal axis and/or slidably move the UTA 420 along a path of the LIMA (e.g., along the disconnect path) so that all selected connective tissue (e.g., situated along the disconnect path) may be fractionated. For example, the controller may distinguish connective tissue which has been fractionated from connective tissue that has not been fractionated along the disconnect path and may be operated to control the UTA 420 to only fractionate the connective tissue which is determined not to have been previously fractionated using any suitable method. For example, the controller may map connective tissue that has been fractionated so that it may be distinguished from tissue that has not been fractionated or may map location and/or orientation (e.g., rotation) of the UTA 420 to determine which connective tissue 425 has been fractionated from that which has not. Further, in some embodiments, the controller may determine which transducers of the UTA to drive so that only the tissue that has not been fractionated may be subject to the histotripsy pulses emitted by the UTA 420.

The side branches of the LIMA may be transluminally cauterized using any suitable method such as by using by high-intensity focused ultrasound (HIFU) pulses that are lower in intensity but longer duration (e.g., when compared to the histotripsy pulses). For example, the histotripsy pulses may be characterized by ultrasound pressure >10 MPa pulse duration: several μs pulse repetition frequency: kHz range (e.g., 1 kHz to 999 kHz)

frequency: 1-10 MHz, including operating between 4-6 MHz.

In accordance with embodiments of the present system, to achieve the high pressures/intensities for histotripsy, the transducer array geometry may be composed of an array of individual spherically focused shells. In accordance with embodiments of the present system, the transducer array geometry may be composed of truncated spherically focused concave shells. These HIFU pulses may be emitted by the UTA using the same or separate transducers which emit the histotripsy pulses and may thermally coagulate tissue and blood to stop or otherwise restrict blood flow for example in fractionated connective tissue.

In accordance with embodiments of the present system, the HIFU pulses may be characterized by:

ultrasound intensity: 100 W/cm$^2$ to 2500 W/cm$^2$ pulse 'on' time: in the range of several seconds (e.g., 5 seconds)

pulse 'off' time: several seconds (e.g., 5 seconds)

frequency: 1-10 MHz, including operating between 1-5 MHz.

It should be noted that in accordance with embodiments of the present system, the pulse off time may be equal to the pulse on time. However, in accordance with further embodiments of the present system, the pulse on time may be different than the pulse off time.

However, in yet other embodiments, a trans-catheter cauterizer may be controlled by the controller to transluminally cauterize the side branches of the LIMA. Further, methods to detach the LIMA from the portion of the surrounding tissue and/or cauterize the side branches of the LIMA are discussed in U.S. patent application Ser. No. 15/119,039, filed Aug. 15, 2016, entitled "SYSTEM FOR PERFORMING INTRALUMINAL HISTOTRIPSY AND METHOD OF OPERATION THEREOF", and in U.S. patent application Ser. No. 15/199,077, entitled "SYSTEM FOR PERFORMING TRANSLUMINAL CORONARY BYPASS AND METHOD OF OPERATION THEREOF", the contents of which are incorporated herein by reference.

With regard to determining locations at which the LIMA is to be removed from portion of the connective tissue 425, cauterized, and/or cut, these locations may be determined by the user and/or process using, for example image processing methods.

In some embodiments, the process may transluminally cauterize side branches of the LIMA and/or detach the LIMA from the surrounding connective tissue 423 for example on both sides of the puncture in the LIMA.

After the LIMA is disconnected from the desired connective tissue 425, the UTA 420 may be removed from the LIMA. For example, FIG. 4D shows the surgical apparatus 400 withdrawing the UTA 420 from the determined puncture location 454 of the LIMA in accordance with embodiments of the present system. The UTA 420 may be slidably withdrawn from the LIMA as illustrated by arrow 431. After completing act 309, the process may continue to act 311.

During act 311, the process may grip the LIMA using any suitable gripping instrument such as the grasping tool which may be manipulated to hold the distal end of the detached LIMA. For example, FIG. 4E shows the apparatus 400 grasping the LIMA (using a grasping tool 458) near the distal end of the LIMA in accordance with embodiments of the present system. During this act, the process may further manipulate a surgical scalpel which may be extended from the apparatus 400 to cut the LIMA at a desired location such as at, or proximate to, the puncture location 454 so as to form a distal end of the LIMA at the cut. In yet other embodiments, the LIMA may be cut away from the puncture location 454 such that the LIMA may be accessed during placement of a graft stent as will be illustratively described further herein.

In accordance with embodiments of the present system, the grasping tool 458 may be extended from a distal end of the apparatus 400 and may be manipulated to grasp the LIMA. The grasping tool 458 may have a gripper such as a plier, anvils, etc. mounted at its distal end. The gripper may be mounted on an arm which provides one or more degrees of freedom and may be controlled by the controller and/or user so as to position and/or orientate the gripper in a desired location and/or orientation. Further, the gripper may be controlled to be opened and/or closed by the user and/or controller. After completing act 311, the process may continue to act 313.

During act 313, the process may detach the portion of the LIMA that has been separated from the connective tissue and steer the distal end of this portion of the LIMA to a desired bypass location (BL) on the LAD and may hold the distal end of the LIMA in position against the LAD. Accordingly, the apparatus 400 may be manipulated (by steering at least the flexible portion 450) to steer the LIMA, which is being gripped by the gripping instrument of the apparatus 400, toward the desired bypass location (BL) on the LAD such that the distal end of the LIMA may be positioned at or against the LAD at the bypass location.

FIG. 4F shows the apparatus 400 placing the distal end of the LIMA at the desired bypass location on the LAD in accordance with embodiments of the present system. This navigation can be performed under direct visual guidance from an endoscope or laparoscope inserted through an adjacent port or using a navigation-assisted surgical method such as via interoperative X-ray. In yet other embodiments, it is envisioned that the apparatus 400 may grasp the LIMA through the puncture which may be slightly situated away from the distal end of the LIMA, if desired. After placing the distal end of the LIMA against the LAD at the bypass location, the apparatus 400 may continue to hold the LIMA in position so that a LIMA-to-LAD coupling may be completed as will be described herein. After completing act 313, the process may continue to act 315.

During act 315, the process may establish an anastomosis (e.g., a coupling) between the LIMA and the LAD at a desired bypass location using any suitable method. The LIMA-to-LAD coupling may establish flow communication (e.g., blood flow) from the LIMA to the LAD. The anastomosis may be achieved using an arterial punch of the apparatus 400 that may be passed through the LAD vessel wall to establish a port for revascularization. Then, an endoluminal stent graft (such as a Jostent™ Graftmaster™ graft stent used for punctured coronary arteries manufactured by Abbot Vascular) may be placed at the interface between the LIMA and the LAD. The graft stent may expand against the walls of the LAD and LIMA to ensure good purchase within each vessel. In addition, it may be fenestrated or a continuous tube as required. In some embodiments multiple interlocking (i.e. a fenestrated stent graft in the LAD with a standard stent interlocking through the fenestration) or branched stent grafts or pre-shaped stent grafts may be used. It is further envisioned that the graft stent may include hooks (such as provided by the Anaconda™ stent system by Vascutek) to facilitate attachment and/or another attachment system may be provided as desired.

In accordance with embodiments of the present system, it is envisioned that a laser arteriectomy device, such as excimer laser-assisted nonocclusive anastomosis (ELANA) laser anastomosis catheter or the like may be used to provide a precise circular cut in the LAD so as to establish a port in the LAD through which the graft stent may pass.

In some embodiments, it is envisioned that the apparatus 400 may pass the arterial punch through the puncture of the LIMA and thereafter puncture the LAD vessel wall to establish a port for revascularization. Thereafter or otherwise as desired, the endoluminal stent graft may access the LIMA via the puncture in the LIMA and may be passed at least partially through an access in the LAD (e.g., a port) so as to be placed at the interface of the LIMA and the LAD. The surgical clip 453 may thereafter be removed from the LIMA so that blood flow may be re-established in the LIMA and the LAD flow coupled thereto to complete the surgical bypass procedure in accordance with embodiments of the present system.

After completing act 315, the process may remove portions of the apparatus 400 that are not required to remain in the thoracic cavity such as the surgical clip 453, the flexible portion 450, etc. and may thereafter continue to act 317 where the process may end.

FIG. 5 shows a detailed view of an interior portion of the coupling between the LIMA and the LAD in accordance with embodiments of the present system. A distal end 507 of stent graft stent 501 may pass through a port 503 in the target artery such that the stent graft 501 is situated between the interface of the LIMA and the LAD. In accordance with embodiments of the present system, the stent graft 501 may be a "standard" continuous stent (i.e., not fenestrated) which is simpler to position and align than a fenestrated stent. Further, in accordance with embodiments of the present system, the stent graft 501 may be a fenestrated stent that has holes, which in positioning are aligned with secondary vessels to ensure blood flow is not interrupted (e.g., the holes in an aortic fenestrated stent may be aligned with the renal arteries). In accordance with further embodiments of the present system, the stent graft stent 501 may be two or more stents which are coupled together before and/or during stent placement as discussed herein including one or more of a standard continuous stent, for example, coupled to one or more of a fenestrated stent. As readily appreciated, in using a fenestrated sent, the fenestrated stent may be positioned in the LAD with the fenestration aligned with a puncture site and a second stent may be positioned in the LIMA to interlock (e.g., or otherwise couple) with the fenestration. In accordance with embodiments of the present system, the positioning of the fenestrated and second stents may be reversed from the positioning described above.

FIG. 6 shows a portion of a system 600 in accordance with embodiments of the present system. For example, a portion of the present system 600 may include a processor 610 (e.g., a controller) operationally coupled to a memory 620, a rendering device that may provide a user interface 630 (e.g., a display), sensors 640, actuators 650, and a user input device 670. The memory 620 may be any type of device for storing application data as well as other data related to the described operation. The application data and other data are received by the processor 610 for configuring (e.g., programming) the processor 610 to perform operation acts in accordance with the present system. The processor 610 so configured becomes a special purpose machine particularly suited for performing in accordance with embodiments of the present system. The sensors may be mounted in various locations as may be desired. For example, in accordance with embodiments of the present system, one or more sensors may be mounted on a catheter in accordance with embodiments of the present system. The sensors may include one or more of imaging sensors, position sensors (e.g., linear, rotational, deflection, etc.), temperature sensors, pressure sensors, flow sensors, status sensors, etc. each of which may provide corresponding information to the controller 610 for further processing.

The operation acts may include configuring the system 600 by, for example, configuring the processor 610 to obtain information from user inputs, the sensors 640, and/or the memory 620 and processing this information in accordance with embodiments of the present system to obtain information related to use of the catheter in accordance with embodiments of the present system. The user input portion 670 may include a keyboard, a mouse, a trackball, rotational wheels, a joystick, and/or other device, including touch-sensitive displays, which may be stand alone or be a part of a system, such as part of a personal computer, a notebook computer, a netbook, a tablet, a smart phone, a personal digital assistant (PDA), a mobile phone, and/or other device for communicating with the processor 610 via any operable link. The user input portion 670 may be operable for interacting with the processor 610 including enabling interaction within a UI as described herein. Clearly the processor 610, the memory 620, the UI 630, the actuators 650, and/or user input device 670 may all or partly be a portion of a computer system or other device such as a client and/or server as described herein.

Operation acts may include requesting, providing, and/or rendering of information such as, for example, information related navigation-assisted imaging information to determine location of one or more portions of the catheter within a patient during surgery. The processor 610 may render the information (e.g., status information) on the UI 630 such as on a display of the system. The processor 610 may render image information (e.g., in real-time) which may include images of a region-of-interest.

The methods of the present system are particularly suited to be carried out by a processor programmed by a computer software program, such as a program containing modules corresponding to one or more of the individual steps or acts described and/or envisioned by the present system.

The processor 610 is operable for providing control signals and/or performing operations in response to input signals from the user input device 670 as well as in response to other devices of a network and executing instructions stored in the memory 620. For example, the processors 610 may obtain feedback information from the sensors 640 and may process this information to determine position, orientation, and/or status of portions of the catheter. The processor 610 may control and/or determine actions to perform in accordance with embodiments of the present system. For example, the processor 610 may control the actuators to perform corresponding actions. The actuators may include motors (e.g., linear, rotational, etc.), pumps, electro-active polymers (EAPs), scalpels (e.g., laser, etc.), ultrasound transducers, lasers, amplifiers, switches, etc. The processor 610 may include one or more of a microprocessor, an application-specific or general-use integrated circuit(s), a logic device, etc. Further, the processor 610 may be a dedicated processor for performing in accordance with the present system or may be a general-purpose processor wherein only one of many functions operates for performing in accordance with the present system. The processor 610 may operate utilizing a program portion, multiple program segments, and/or may be a hardware device utilizing a dedicated or multi-purpose integrated circuit.

While the present invention has been shown and described with reference to particular exemplary embodiments, it will be understood by those skilled in the art that present invention is not limited thereto, but that various changes in form and details, including the combination, separation and/or deletion of various features and/or elements may be made therein without departing from the spirit and scope of the present system.

Accordingly, embodiments of the present system provide a flexible apparatus and method thereof to access the thoracic cavity via a minimally invasive incision, remove the distal LIMA from the chest wall using ultrasound, direct the LIMA towards a selected area on the diseased coronary artery, and attach the LIMA to the bypass site. For example, in accordance with embodiments of the present system, an optimal coronary revascularization may be provided that combines effectiveness of LIMA-LAD bypass with a minimally invasive approach of stenting.

The use of a flexible apparatus including a UTA driven in accordance with embodiments of the present system within the graft vessel may eliminate the need for the operator to dissect the LIMA from the tissue bed thereby saving time, reducing the likelihood of damaging the LIMA during harvesting, and/or reduce the size of surgical access sites required to access the LIMA for harvesting. In this way, embodiments of the present system may provide benefits having a positive impact on patient recovery.

Further variations of the present system would readily occur to a person of ordinary skill in the art and are encompassed by the following claims.

Finally, the above-discussion is intended to be merely illustrative of the present system and should not be construed as limiting the appended claims to any particular embodiment or group of embodiments. Thus, while the present system has been described with reference to exemplary embodiments, it should also be appreciated that numerous modifications and alternative embodiments may be devised by those having ordinary skill in the art without departing from the broader and intended spirit and scope of the present system as set forth in the claims that follow. In addition, the section headings included herein are intended to facilitate a review but are not intended to limit the scope of the present system. Accordingly, the specification and drawings are to be regarded in an illustrative manner and are not intended to limit the scope of the appended claims.

The specification and drawings are to be regarded in an illustrative manner and are not intended to limit the scope of the appended claims.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function;

e) any of the disclosed elements may be comprised of hardware portions (e.g., including discrete and integrated electronic circuitry), software portions (e.g., computer programming), and any combination thereof;

f) hardware portions may be comprised of one or both of analog and digital portions;

g) any of the disclosed devices or portions thereof may be combined together or separated into further portions unless specifically stated otherwise;

h) no specific sequence of acts or steps is intended to be required unless specifically indicated; and i) the term "plurality of" an element includes two or more of the claimed element, and does not imply any particular range of number of elements; that is, a plurality of elements may be as few as two elements, and may include an immeasurable number of elements.

The invention claimed is:

1. An apparatus for performing a bypass procedure, the apparatus comprising:
    a flexible body defining a plurality of channels configured to receive one or more instruments slidably deployable through corresponding channels of the plurality of channels, one of the instruments comprising an ultrasound transducer array; and
    at least one controller configured to:
        drive at least one transducer of the transducer array extending from one of the plurality of channels into a first artery to transluminally detach at least a portion of a first artery from connective tissue of a chest wall;

enable steering the flexible body of the apparatus that is located outside of the first artery to move at least a portion of the detached portion of the first artery from a current location to a bypass location at a target artery; and enable coupling of the first artery to the target artery at the bypass location to establish flow communication between the first artery and the target artery.

2. The apparatus of claim 1, wherein the at least one controller is further configured to enable placement of a clip, deployable through another one of the plurality of channels, about the first artery, the clip being configured to interrupt blood flow to the first artery.

3. The apparatus of claim 1, wherein the at least one controller is further configured to enable establishing a port in the target artery at the bypass location using one of an arterial puncture device and a laser arteriectomy device deployable through another one of the plurality of channels.

4. The apparatus of claim 3, wherein the at least one controller is further configured to enable insertion of a graft stent, deployable through another one of the plurality of channels, at least partially through the port in the target artery.

5. The apparatus of claim 1, wherein the at least one controller is further configured to drive the at least one transducer such that the ultrasound signals of a first type comprise histotripsy pulses and the ultrasound signals of a second type comprise high-intensity focused ultrasound (HIFU) pulses that are lower in intensity and longer in duration than the ultrasound signals of the first type.

6. The apparatus of claim 5, wherein the at least one controller is further configured to enable transluminally cauterizing side branches of the first artery by applying the ultrasound signals of the second type emitted by the at least one transducer.

7. The apparatus of claim 5, wherein the at least one controller is further configured to enable transluminally detaching the portion of the first artery from connective tissue of a chest wall that is attached to the first artery by applying the ultrasound signals of the first type emitted by the at least one transducer.

* * * * *